US010722613B2

(12) United States Patent
Ashworth et al.

(10) Patent No.: US 10,722,613 B2
(45) Date of Patent: Jul. 28, 2020

(54) METHOD OF PREPARING CALCIFICATION-RESISTANT BIOPROSTHETIC TISSUE

(71) Applicant: St. Jude Medical, Cardiology Division, Inc., St. Paul, MN (US)

(72) Inventors: Paul E. Ashworth, Wyoming, MN (US); Chad Joshua Green, Forest lake, MN (US); Jay Reimer, Saint Paul, MN (US); Katherine A. Ahmann, Arden Hills, MN (US); David A. Panus, Maple Grove, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 145 days.

(21) Appl. No.: 16/023,436

(22) Filed: Jun. 29, 2018

(65) Prior Publication Data
US 2019/0001023 A1  Jan. 3, 2019

Related U.S. Application Data

(60) Provisional application No. 62/526,492, filed on Jun. 29, 2017.

(51) Int. Cl.
*A61L 27/36* (2006.01)
*A61F 2/24* (2006.01)
*A61L 27/50* (2006.01)

(52) U.S. Cl.
CPC .......... *A61L 27/3687* (2013.01); *A61F 2/24* (2013.01); *A61L 27/3695* (2013.01);
(Continued)

(58) Field of Classification Search
CPC .......... A61L 27/3604; A61L 27/3687; A61L 27/507; A61L 27/3629; A61L 27/3625;
(Continued)

(56) References Cited

U.S. PATENT DOCUMENTS 4,629,459 A * 12/1986 Ionescu ................ A61F 2/2412
623/2.15
5,002,566 A    3/1991 Carpentier et al.
(Continued)

FOREIGN PATENT DOCUMENTS

EP    3296391 A1    3/2018
WO    199966967 A1    12/1999
WO    2016180259 A1    11/2016

OTHER PUBLICATIONS

International Search Report for PCT/US2018/040215 and Written Opinion, dated Oct. 2, 2018.

*Primary Examiner* — Samuel G Gilbert
(74) *Attorney, Agent, or Firm* — Lerner, David, Littenberg, Krumholz & Mentlik, LLP

(57) ABSTRACT

Methods of preparing calcification-resistant bioprosthetic tissue include providing fresh biological tissue, cross-linking the tissue, treating the cross-linked tissue with an alcohol for a time sufficient to allow the alcohol to be diffused into the tissue, and treating the alcohol-treated fixed tissue with a polyol for a time sufficient to allow fluid in the tissue to be replaced by the polyol. The methods may include sterilizing the cross-linked tissue in a solution including propylene oxide or peracetic acid either before or after the alcohol treatment step; or drying the alcohol/polyol-treated, cross-linked tissue, sterilizing the dried tissue by exposure to ethylene oxide or peracetic acid, and storing the sterilized tissue in a dry, ambient environment. The treated tissue may be a tissue component for a bioprosthetic valve, a valve assembly for a bioprosthetic valve or a fully assembled bioprosthetic valve incorporating the tissue.

23 Claims, 2 Drawing Sheets

(52) U.S. Cl.
CPC ......... *A61L 27/507* (2013.01); *A61L 2400/02* (2013.01); *A61L 2430/40* (2013.01)

(58) Field of Classification Search
CPC ...... A61L 27/3691; A61F 2/24; A61F 2/2412; A61F 2/0095; A61F 2/2415; A61F 2/2418
See application file for complete search history.

(56) References Cited

U.S. PATENT DOCUMENTS

| | | | |
|---|---|---|---|
| 5,476,516 A | 12/1995 | Seifter et al. | |
| 5,489,298 A * | 2/1996 | Love | A61F 2/2472 623/2.14 |
| 5,746,775 A | 5/1998 | Levy et al. | |
| 5,862,806 A | 1/1999 | Cheung | |
| 6,096,347 A * | 8/2000 | Geddes | A61K 35/12 424/551 |
| 6,521,179 B1 * | 2/2003 | Girardot | A01N 1/00 422/28 |
| 6,534,004 B2 | 3/2003 | Chen et al. | |
| 7,972,376 B1 | 7/2011 | Dove et al. | |
| 8,748,490 B2 | 6/2014 | Dove et al. | |
| 2009/0164005 A1 * | 6/2009 | Dove | A61L 27/3604 623/2.13 |

\* cited by examiner

METHOD OF PREPARING CALCIFICATION-RESISTANT BIOPROSTHETIC TISSUE

CROSS-REFERENCE TO RELATED APPLICATIONS

The present application claims the benefit of the filing date of U.S. Provisional Patent Application No. 62/526,492 filed Jun. 29, 2017, the disclosure of which is hereby incorporated herein by reference.

BACKGROUND OF THE INVENTION

The present disclosure is directed to prosthetic medical devices, in particular, prosthetic heart valves. More particularly, the present disclosure is directed to prosthetic heart valves formed from biological tissue, and to the treatment of such tissue to resist calcification.

Bioprosthetic tissue is often used in bioprosthetic devices or to repair damaged tissue in a patient. For example, it has become common practice to replace damaged or diseased native heart valves with bioprosthetic valves. The bioprosthetic valve, which is also generally known as a "tissue valve," may be made with tissue of biological origin, such as tissue of porcine or bovine origin. Such valves are less likely to cause blood clotting and have improved hemodynamic properties compared to mechanical valves that may be made of metal or synthetic polymeric materials.

The most common cause for the failure of implanted bioprosthetic devices is in vivo calcification. The mechanism of calcification of bioprosthetic tissue is not fully understood. Calcification may be due to host factors, implant factors, and extraneous factors such as mechanical stress. Certain components within the bioprosthetic tissue, such as phospholipids, cholesterol, collagen and elastin, are known to be susceptible to calcification. They can become calcified following the implantation of bioprosthetic valves. The calcification can result in undesirable stiffening or degradation of the bioprosthesis, which leads to device failure.

Typically prior to implantation, the biological tissue is chemically cross-linked or fixed with agents such as glutaraldehyde or formaldehyde in order to prevent rejection when implanted into a recipient, to provide sterilization, and to help stabilize the proteins in the tissue, thereby making the tissue and the bioprosthetic device containing such tissue more durable to withstand prolonged use and millions of cycles of opening and closing under circulatory pressure without fatigue. Glutaraldehyde is the most commonly used fixative that can be applied at a physiological pH under aqueous conditions for preparing tissue for implantation. Unfortunately, glutaraldehyde is now known to promote in vivo calcification. The unstable glutaraldehyde creates potential calcium binding sites within the tissue that can lead to calcification.

Various techniques have been developed in the treatment of bioprosthetic tissue for mitigating in vivo calcification. One such attempt, disclosed in U.S. Pat. No. 5,002,566 to Carpentier et al., involves a pretreatment of glutaraldehyde-fixed bioprosthetic tissue with a calcification-inhibiting amount of ferric or stannic ions or a mixture thereof. The CARPENTIER-EDWARDS ThermaFix™ tissue process is an FDA-approved anti-calcification treatment of bioprosthetic tissue that reduces the calcium binding sites by a two-step process, with a first thermal treatment to remove up to 81 percent of the unstable glutaraldehyde and a second chemical treatment to remove 98 percent of the phospholipids. In U.S. Pat. No. 5,476,516, Seifter et al. disclose a method of treating aldehyde-fixed biological tissue with a liquid polyol to minimize in vivo calcification. The polyol is at least 60% in a solution, and preferably solvent-free. Levy et al., in U.S. Pat. No. 5,746,775, discloses a tissue anti-calcification process for a collagenous biomaterial in which the biomaterial is exposed to an alcohol to inhibit calcification. The biomaterial, preferably glutaraldehyde-pretreated, is subjected to an aqueous solution of 60% to 80% of a lower aliphatic alcohol, such as ethanol, for a period of at least 20 minutes, and preferably, 24 to 72 hours. The biomaterial is then rinsed, and stored in a glutaraldehyde solution or ethanol-glutaraldehyde solution. This process reduces the toxicity of glutaraldehyde, and removes 99 percent of the cholesterol and 94 percent of the phospholipids in bioprosthetic tissue, resulting in resistance to calcification in various preclinical models.

To prevent the transmission of disease-causing microorganisms to the device recipient, the tissue and the bioprosthetic device made therefrom should be sterile. The bioprosthetic device should be stored in a sterile and stable condition from manufacture until use. For example, bioprosthetic heart valves, including surgical and transcatheter heart valves, are typically sterilized and stored in an aldehyde solution (i.e., glutaraldehyde or formaldehyde) prior to use. These solutions help keep the tissue in a hydrated state and kill any microbes that may be attached to the tissue. However, both glutaraldehyde and formaldehyde are irritants and have some inherent level of toxicity. Glutaraldehyde is also known to contribute to in vivo calcification. A bioprosthetic device that is stored in such a solution therefore must be extensively rinsed to remove any residual aldehydes prior to implantation.

Attempts have been made to develop a bioprosthetic valve that is in a substantially "dry" form, substantially free of glutaraldehyde or formaldehyde, and ready for implantation with minimal preparation prior to surgery. Chen et al., in U.S. Pat. No. 6,534,004, disclose a process for dry storing bioprosthetic devices comprising a tissue component. The process includes treating the fixed tissue component with an aqueous solution comprising dimensional stabilizers such as polyhydric alcohols or their derivatives. Another strategy, described in U.S. Pat. No. 8,748,490 to Dove et al., is to dehydrate the bioprosthetic tissue in a glycerol/ethanol mixture. However, such dehydration processes do not provide the tissue with calcification resistance.

Bioprosthetic tissue in the "dry" form is usually sterilized with ethylene oxide, gamma irradiation, or electron beam irradiation. However, ethylene oxide sterilization requires the tissue to be exposed to increased temperatures and water vapor which may damage or rehydrate the tissue. Gamma irradiation is known to cause backbone scission and breakage of collagen fibrils, leading to decreased mechanical and biochemical functionality in the tissue. Electron beam irradiation will also cleave the collagen backbone and lead to deterioration of the tissue structure and reactivity. These types of damage during sterilization and/or storage may contribute to valve deterioration and structural failure.

Therefore, there is a continuing need to develop a method of preparing bioprosthetic tissue or a bioprosthetic device containing such tissue so as to minimize in vivo calcification and allow for sterilization and storage in a non-toxic environment without causing damage to the tissue.

BRIEF SUMMARY OF THE INVENTION

The present disclosure relates to methods of preparing calcification-resistant bioprosthetic tissue or a bioprosthetic device containing such tissue, wherein the tissue, preferably pre-fixed bioprosthetic tissue, is treated with a two-step process, an alcohol treatment followed by exposure to a polyol. The two-step treatment process minimizes in vivo calcification and reduces cytotoxicity without impairing the mechanical strength of the fixed bioprosthetic tissue. The processed tissue when wet may be sterilized and/or stored using an appropriate method that is compatible with the wet tissue. Preferably, the processed wet tissue may be sterilized and stored in a non-toxic solution containing propylene oxide (which converts to non-toxic propylene glycol during sterilization and storage).

The process preferably further comprises the step of drying the alcohol/polyol-treated fixed tissue at ambient conditions or under vacuum, and the resultant tissue or device made therefrom can be stored in a dry ambient condition. These methods thus provide the advantages of producing tissue or devices containing such tissue with reduced size, volume and weight compared to bioprosthetic tissue or devices stored in a fluid medium; eliminating toxic fluid associated with the tissue or device storage; and reducing changes or damage to the tissue during the drying process. The processed tissue when dried may be sterilized using an appropriate method that is compatible with the dry tissue. Preferably, the processed dry tissue may be sterilized by exposure to ethylene oxide gas or peracetic acid gas. Prior to use, the tissue or the device comprising the same is optionally rinsed or rehydrated, such as by a sterile 0.9 wt % aqueous saline solution.

The present disclosure describes methods of preparing biological tissue that is resistant to in vivo calcification, and therefore has good mechanical stability and durability. The tissue is for use in bioprosthetic devices or other heterograft applications. In one embodiment, the bioprosthetic device is a bioprosthetic heart valve.

In one embodiment, the method comprises the steps of fixing fresh biological tissue; treating the fixed tissue with an alcohol for a time sufficient to allow the alcohol to be diffused into the tissue; and treating the alcohol-treated fixed tissue with a polyol for a time sufficient to allow the fluid in the tissue to be replaced by the polyol. The alcohol is preferably a lower aliphatic alcohol ($C_1$ to $C_8$) which includes, but is not limited to, methanol, ethanol, propanol, isopropanol, pentanol, octanol, or a combination thereof. More preferably, the alcohol is ethanol. The alcohol is preferably in an aqueous solution comprising from about 85 v/v % to about 100 v/v % of alcohol (i.e., a neat alcohol); and more preferably, about 95 v/v % of alcohol. The polyol is preferably a lower aliphatic diol or triol ($C_1$ to $C_4$) which includes, but is not limited to, ethylene glycol, propylene glycol, butylene glycol, glycerol, or a combination thereof. More preferably, the polyol is glycerol. The polyol is preferably in a 0.9 wt % aqueous saline solution comprising about 20 v/v % to about 100 v/v % of polyol (i.e., a neat polyol), and more preferably, about 50 v/v % of polyol. In one embodiment, the alcohol/polyol-treated fixed tissue is stored in an aqueous solution. The processed tissue when wet may be sterilized using an appropriate sterilization method that is compatible with wet tissue.

Preferably, the method further comprises placing the alcohol/polyol-treated fixed tissue at an ambient condition or under vacuum for drying; and storing the dried tissue in a dry ambient condition. In another embodiment, the processed tissue when dried may be sterilized using an appropriate sterilization method that is compatible with dry tissue.

The tissue may be in the form of a tissue component for a bioprosthetic device or other heterograft applications. The device may be a valve assembly for a bioprosthetic heart valve, or a fully assembled bioprosthetic heart valve incorporating the tissue.

The present disclosure also relates to tissue, a bioprosthetic device or a packaged bioprosthetic device containing the same, wherein the tissue is prepared by the processing methods described above.

BRIEF DESCRIPTION OF THE DRAWINGS

These and other features, aspects, and advantages of the present disclosure will become better understood with regard to the following description, appended claims, and accompanying drawings in which:

DETAILED DESCRIPTION

Figure 1:
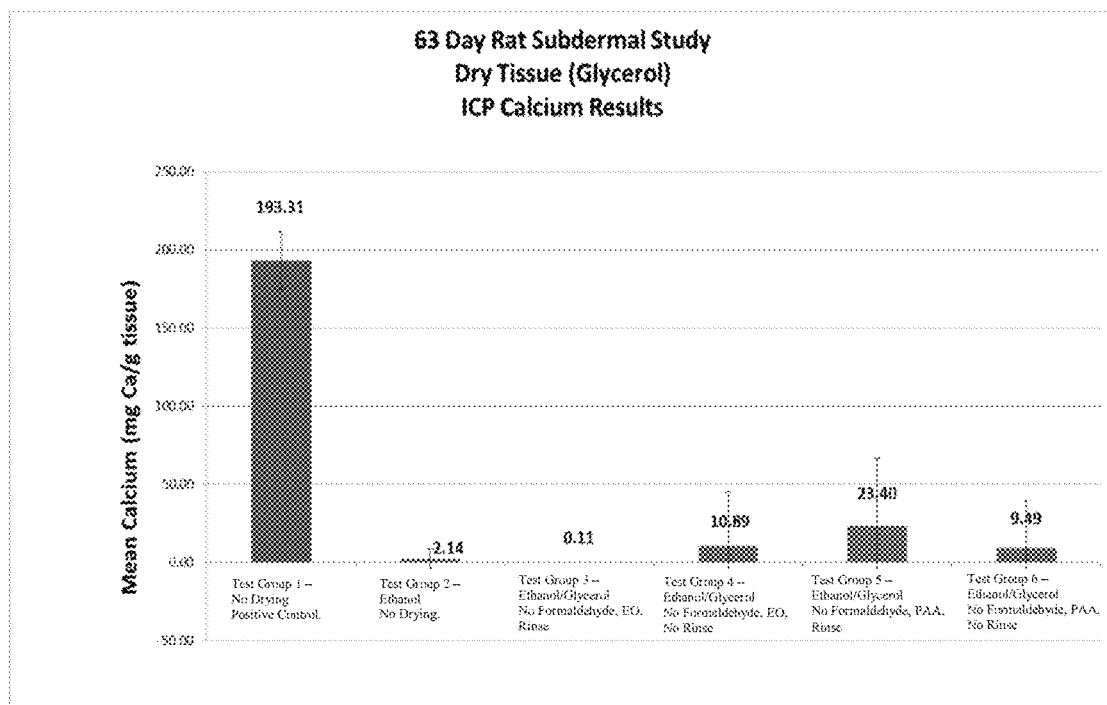
FIG. 1 is a bar graph depicting the mean calcium of Test Groups 1-6 in a 63-day rat subdermal study.

Before describing at least one embodiment of the present disclosure in detail, it is to be understood that the present disclosure is not limited in its application to the details set forth in the following description or exemplified by the examples. Aspects of the present disclosure are capable of other embodiments or of being practiced or carried out in various ways. Also, it is to be understood that the phrasing and terminology employed herein is for the purpose of description and should not be regarded as limiting.

The present disclosure provides a method of preparing bioprosthetic tissue or a bioprosthetic device comprising such tissue so as to have strong calcification resistance and allow for sterilization and storage in a non-toxic environment without causing damage to the tissue. Bioprosthetic valves, which are also generally known as "tissue valves," are prosthetic valves made with at least some tissue of biological origin. "Biological tissue" or "tissue," as used herein, refers to biological tissue dissected from an animal, typically a mammalian species such as, for example, porcine or bovine tissue. Specific tissue types that may be used include, without limitation, any blood vessel, pericardial tissue, heart muscle tissue, dura matter and the like. More than one species and tissue type may be used in a valve assembly. "Fixed" or "cross-linked" tissue refers to tissue in which the proteins have reduced solubility, antigenicity, and biodegradability as compared to the proteins in the native tissue. "Fixing" or "cross-linking" can be accomplished by a number of techniques, for example, by treatment with aldehydes, epoxides, carbodimides or genipin, or by photo fixation. Conventionally, fixing can be performed by cross-linking the amine groups of the tissue proteins with an aldehyde, such as about 0.001 v/v % to about 5 v/v % glutaraldehyde or formaldehyde solution. The term "valve" as used herein refers to a complete and operable structure capable of being implanted into a patient to control the flow of blood through the patient's circulatory system. A valve can be a surgical valve, a transcatheter valve or any other non-native (i.e., prosthetic) valve structure. The terms "implanted" or "implantation," as used herein, refer to a complete and long-term seating of a valve in a patient. A "valve assembly" as used herein is a structure that is made, at least in part, from tissue, and that operates to meter or restrict blood flow for at least some period of time, but does not include other structures like a stent often used to support the valve assembly. Thus, a tissue valve for purposes of the present description is a bioprosthetic valve that includes at least a valve assembly. The tissue valve may, and often does, include other structures, such as a supporting stent. As used herein, the terms "about," "generally," "substantially" and the like are intended to mean that slight deviations from absolute are included within the scope of the term so modified. Bioprosthetic valves in accordance with the present disclosure may be used in the heart as a replacement for one of the native cardiac valves, such as the aortic valve or mitral valve, but are not limited thereto and can be used in other structures, including blood vessels.

In one embodiment, fresh biological tissue is first fixed or crossed-linked. Fixing or cross-linking can be accomplished by a number of techniques, for example, by cross-linking with epoxides, carbodimides or genipin, or photo fixation. Conventionally, fixing can be accomplished by cross-linking the amine groups of the tissue proteins with an aldehyde, such as a solution of about 0.001 v/v % to about 5 v/v %, preferably about 0.2 v/v % to about 0.8 v/v %, more preferably about 0.5 v/v %, of glutaraldehyde or formaldehyde in a solvent for about several hours to several weeks. In some embodiments, the solvent may be water or a 0.9 wt % aqueous saline solution. In other embodiments, the solvent may be either a phosphate-buffered solution such as phosphate-buffered saline (PBS), or preferably, a phosphate-free buffer. Phosphate-free buffers include, but are not limited to, borate, carbonate, bicarbonate, citrate, cacodylate, and other synthetic buffers such as N-2-Hydroxyethyl-piperazine-N'-2-ethanesulphonic acid (HEPES), 2-(N-morpholino)-propane-sulphonic acid (MOPS) and 1,4-piperazinebis(Ethanesulphonic acid) (PIPES). Glutaraldehyde is the most commonly used fixative that can be applied at a physiological pH under aqueous conditions for preparing tissues for implantation. In one embodiment, the fresh biological tissue may be exposed to a glutaraldehyde solution in a preferred concentration noted above at a temperature from about 4° C. to about 25° C. and a pH from about 6 to about 8, preferably from about 7.1 to about 7.8. The fixed tissue is optionally rinsed thoroughly with a sterile 0.9 wt % aqueous saline solution to substantially reduce the amount of unreacted fixative within the tissue. Thereafter, the fixed tissue is further processed immediately or stored in an aqueous solution until further processing to prevent drying out and shrinkage of the fixed tissue.

In one embodiment, the aqueous storage solution may comprise about 0.001 v/v % to about 10 v/v %, preferably about 0.5 v/v %, of glutaraldehyde or formaldehyde. In another embodiment, the aqueous storage solution may be sterile saline. A saline solution is generally composed of distilled and/or deionized water with sodium chloride in a concentration ranging from about 0.01 wt % to about 1.5 wt %. More specifically, the sodium chloride concentration can range from about 0.75 wt % to about 1.05 wt %, and preferably is about 0.9 wt %. Isotonic saline is often used. As an alternative to sodium chloride, the following salts may be used for the saline solution: potassium chloride, calcium chloride, magnesium sulfate, disodium phosphate, sodium bicarbonate, magnesium chloride, sodium phosphate, potassium phosphate, or any combination thereof, with or without sodium chloride. Additionally, the saline solution may be a balanced salt solution such as Hank's, Earle's, Gey's or Ouck's balanced salt solution, or may be a phosphate buffered solution. Treating the tissue with a saline solution may assist in leaching organic solvents or residue from the tissue.

After the fixing step (or after removal from the aqueous storage solution), the tissue optionally can be sterilized using an appropriate method that is compatible with the wet tissue. Such method includes, but is not limited to, using various solutions, such as aldehydes, alcohols, epoxides, a combination thereof, or other various antimicrobial solutions, for liquid chemical sterilization. In one embodiment, the processed wet tissue can be sterilized and stored in a standard aldehyde solution, such as a glutaraldehyde or formaldehyde solution that is typically used for long-term sterilization and storage of clinical-grade bioprostheses, preferably at a concentration of about 0.2 v/v % to about 0.8 v/v %, more preferably at a concentration of about 0.5 v/v % of aldehyde in water, in a 0.9 wt % aqueous saline solution, in a phosphate-buffered solution, or in a phosphate-free buffered solution. In one preferred embodiment, the processed wet tissue can be sterilized and stored in a solution containing propylene oxide or peracetic acid. The solution may include propylene oxide or peracetic acid in buffered or unbuffered water or in a 0.9 wt % aqueous saline solution. Propylene oxide is more biocompatible compared to conventional antimicrobial solutions containing aldehydes. The propylene oxide solution is preferably a solution containing about 1% to about 10% propylene oxide, preferably about 2% propylene oxide. In one embodiment, the sterilization and storage solution is buffered to a pH between about 6.0 and about 8.0, and preferably between about 7.1 and about 7.8, and more preferably about 7.4. Suitable buffers for use in these solutions are those buffers that have a buffering capacity sufficient to maintain a physiologically acceptable pH and that do not cause any deleterious effects to the bioprosthetic tissue or interfere with the treatment process. Exemplary buffers include, but are not limited to, phosphate-buffered saline (PBS), and phosphate-free buffers such as borate, carbonate, bicarbonate, citrate, cacodylate, N-2-Hydroxyethylpiperazine-N'-2-ethanesulphonic acid (HEPES), 2-(N-morpholino)-propane-sulphonic acid (MOPS) and 1,4-piperazinebis(Ethanesulphonic acid) (PIPES).

The fixed tissue (before or after sterilization) may be treated with an alcohol. Preferably, the alcohol is a lower aliphatic alcohol ($C_1$ to $C_8$) which includes, but is not limited to, methanol, ethanol, propanol, isopropanol, pentanol, octanol, or a combination thereof. More preferably, the alcohol is ethanol. The manner in which the fixed tissue is exposed to the alcohol includes, but is not limited to, vapor, plasma, liquid, and cryogenic application of the alcohol. Preferably, the tissue is treated with an alcohol solution. More preferably, the alcohol solution is an aqueous solution comprising from about 85 v/v % to about 100 v/v % of alcohol (i.e., a neat alcohol); and most preferably, about 95 v/v % of alcohol. In one embodiment, the aqueous alcohol solution may be buffered to a pH between about 6.0 and about 8.0, and preferably between about 7.1 and about 7.8, and more preferably about 7.4. Suitable buffers for use in this step are those buffers that have a buffering capacity sufficient to maintain a physiologically acceptable pH and that do not cause any deleterious effects to the bioprosthetic tissue or interfere with the treatment process. Exemplary buffers include, but are not limited to, phosphate-buffered saline (PBS), and phosphate-free buffers such as borate, carbonate, bicarbonate, citrate, cacodylate, N-2-Hydroxyethylpiperazine-N'-2-ethanesulphonic acid (HEPES), 2-(N-morpholino)-propane-sulphonic acid (MOPS) and 1,4-piperazinebis(Ethanesulphonic acid) (PIPES).

The tissue component may be exposed to, or contacted with, the alcohol for a time and at a temperature sufficient to permit the alcohol to penetrate into the interstices of the tissue by passive diffusion and replace the fluid therein. The time needed to achieve such replacement is directly related to the thickness of the tissue, and inversely related to the ratio between the volume of the alcohol or alcohol solution and the volume of the tissue. Tissue having a thickness between about 0.05 mm and about 2 mm may be contacted with an alcohol solution at a temperature between about 4° C. and about 37° C. for about 12 hours to about 48 hours; preferably, for about 24 hours. More preferably, such tissue may be contacted with an alcohol solution at room temperature for about 24 hours.

The tissue may be contacted with the alcohol solution by a standard method, such as by immersion in the solution. The amount of the alcohol solution is at least sufficient to submerge the tissue. Preferably, the volume of the alcohol solution is at least about 2 times the volume of the tissue that is brought into contact with the solution; more preferably, about 50 times the volume of the tissue; and still more preferably, about 100 times the volume of the tissue.

In one embodiment, the tissue may be shaken or agitated during the alcohol treatment. Shaking can be accomplished in any manner, such as through the use of an orbital shaker, or a shaker stand.

After exposure to the alcohol for a sufficient time, the tissue is removed from the alcohol and optionally rinsed with a sterile 0.9 wt % aqueous saline solution. The alcohol-treated fixed tissue may then be treated with a polyol. Preferably, the polyol is a lower aliphatic diol or triol ($C_1$ to $C_4$) which includes, but is not limited to, ethylene glycol, propylene glycol, butylene glycol, glycerol, or a combination thereof. More preferably, the polyol is glycerol. Preferably, the alcohol-treated, fixed tissue is treated with a polyol solution. The polyol may be in solution with water or with a 0.9 wt % aqueous saline solution, and may comprise from about 20 v/v % to about 100 v/v % of polyol (i.e., a neat polyol); and preferably, about 50 v/v % of polyol. A solution of polyol in a 0.9 wt % aqueous saline solution is preferred. In one embodiment, a solution of polyol in water may be buffered to a pH between about 6.0 and about 8.0, preferably between about 7.1 and about 7.8, and more preferably about 7.4. Suitable buffers for use are those buffers that have a buffering capacity sufficient to maintain a physiologically acceptable pH and that do not cause any deleterious effects to the bioprosthetic tissue or interfere with the treatment process. Exemplary buffers include, but are not limited to, phosphate-buffered saline (PBS), and phosphate-free buffers such as borate, carbonate, bicarbonate, citrate, cacodylate, N-2-Hydroxyethylpiperazine-N'-2-ethanesulphonic acid (HEPES), 2-(N-morpholino)-propane-sulphonic acid (MOPS) and 1,4-piperazinebis(Ethanesulphonic acid) (PIPES).

The tissue component may be exposed to, or contacted with, the polyol for a time and at a temperature sufficient to permit the polyol to penetrate into the interstices of the tissue by passive diffusion and replace the fluid therein. The time needed to achieve such replacement is directly related to the thickness of the tissue, and inversely related to the ratio between the volume of the polyol or polyol solution and the volume of the tissue. Tissue having a thickness between about 0.05 mm and about 2 mm may be contacted with a polyol solution at a temperature between about 4° C. and about 37° C. for about 12 hours to about 48 hours; preferably, for about 24 hours. More preferably, such tissue may be contacted with a polyol solution at room temperature for about 24 hours.

The tissue may be contacted with the polyol solution by a standard method, such as by immersion in the solution. The amount of the polyol solution is at least sufficient to submerge the tissue. Preferably, the volume of the polyol solution is at least about 2 times the volume of the tissue that is brought into contact with the solution; more preferably, about 50 times the volume of the tissue; and still more preferably, about 100 times the volume of the tissue. The tissue may be shaken or agitated in any manner during the polyol treatment, such as the manners described above for use during the alcohol treatment.

After soaking in the polyol solution for a sufficient time, the tissue is removed from the polyol solution and optionally rinsed with a sterile 0.9 wt % aqueous saline solution. It then may be placed in an aqueous solution for storage until use. The aqueous storage solution is described above. In one embodiment, the alcohol/polyol-treated fixed tissue can be stored in a package with an aqueous solution.

The treated, fixed, wet tissue (with or without sterilization before the alcohol treatment step) may be sterilized after the polyol treatment using an appropriate method that is compatible with the wet tissue. Preferably, only if not sterilized before the alcohol treatment step, the treated, fixed, wet tissue may be sterilized after the polyol treatment using an appropriate method that is compatible with the wet tissue. Any of the methods described above for the sterilization of wet tissue after the fixing step may be used.

Preferably, the method further comprises placing the alcohol/polyol-treated fixed tissue in an ambient condition or under vacuum for drying; and storing the dry tissue in a dry ambient condition. The alcohol/polyol-treated fixed tissue may be exposed to ambient air at a temperature from about 15° C. to about 25° C. and a relative humidity from about 10% to about 30% for at least four hours to remove the aqueous solution. Preferably, the alcohol/polyol-treated fixed tissue is exposed to ambient air at room temperature for about 12 hours.

In one embodiment, the alcohol/polyol-treated fixed tissue may be placed in a jar or other container for vacuum drying. Vacuum drying is a process in which materials are dried in a reduced pressure environment, which lowers the heat needed for rapid drying. As such, vacuum-drying tends to retain the integrity of the original item with less damage. A vacuum is applied to the container having the tissue inside for a time sufficient to remove substantially all the fluid in the tissue, without the application of heat. The vacuum pressure is no more than about 1000 mTorr, preferably no more than about 200 mTorr, and more preferably no more than about 10 mTorr. The tissue can be subjected to vacuum drying for about one minute to about 2 months. Preferably, a vacuum of about 5 mTorr is applied to the container for at least 4 hours. More preferably, a vacuum of about 5 mTorr is applied to the container for about 6 to about 24 hours.

The alcohol/polyol treatment of the tissue and the drying steps described above may be performed on individual tissue components for the valve assembly, on a valve assembly, or on a completed tissue valve. Thus, individual tissue components may be subjected to the alcohol/polyol treatment steps before or after formation of the valve assembly but prior to the fabrication of the tissue valve, or after fabrication of the tissue valve. In one embodiment, the individual tissue components may be tissue patches for use in cardiac repairs. Such tissue patches prepared using the alcohol/polyol treatment steps described herein may advantageously have strong calcification resistance.

Air-drying or vacuum-drying of the alcohol/polyol-treated fixed tissue can occur before or after construction of a valve assembly or before or after construction of a tissue valve. Thus, in one embodiment, the alcohol/polyol-treated "wet" fixed tissue (bioprosthetic fixed tissue treated with an alcohol followed by a polyol) may be air-dried or vacuum-dried and then stored dry until needed for manufacture. The tissue may be rehydrated prior to being manufactured into a valve assembly, and may then be air-dried or vacuum-dried again for storage. In another embodiment, the alcohol/polyol-treated "wet" fixed tissue may be attached to a support or stent to construct a valve assembly on the support and thereafter the entire resulting tissue valve may be air-dried or vacuum-dried prior to storage. In yet another embodiment, the alcohol/polyol-treated "wet" fixed tissue may be used to construct a "wet" valve assembly without a support. This "wet" valve assembly can be stored in an aqueous solution. It can also be air-dried or vacuum-dried, and then attached to a support; or attached to the support first, followed by air-drying or vacuum-drying of the resulting tissue valve.

The construction of a valve assembly or a tissue valve can involve general techniques used in the art. An example of a method of constructing a tissue valve includes attaching a valve assembly comprised of at least one leaflet to a support or stent configured to fit within the relevant structure within the patient. The support could either have a fixed size in the case of a surgical valve, or could be collapsible in the case of a transcatheter valve implanted using a minimally invasive procedure.

Due to the removal of fluid from the bioprosthetic tissue during the air-drying or vacuum-drying process, the resulting "dry" bioprosthetic valve has a reduced size, volume and weight when compared to a tissue valve that was stored in a fluid medium. Normally, the weight of "dry" bioprosthetic tissue is at least about 50%, preferably about 75-80%, less than the weight of the same tissue in the wet state.

The method of producing tissue valves for dry storage in the present application eliminates the use of toxic fluids associated with the storage of valves and the subsequent rinsing process, which may make the manufacture and transport of the valves less expensive, may make storage and use more convenient, and may result in less chemical waste to dispose of. It also may reduce the time spent in the operating room preparing the tissue valve for implantation.

Since the tissue valves prepared by the methods described herein do not need to be shipped or stored in a solution to prevent the tissue from drying out, they may be preloaded onto delivery devices, with the entire assembly being provided in sterile packaging such that the valves are able to be reconstituted before use.

The dry tissue component, or the valve assembly or bioprosthetic valve comprising the dry tissue component, wherein the tissue has been treated with alcohol after fixing followed by polyol treatment, may be stored in an environment essentially free of liquid for later processing or implantation. An environment, container or package that is "essentially free of liquid" as used herein means an environment in which the presence of water or other liquids is limited to the content of such liquids in the ambient air (as more precisely expressed as the relative humidity), and the content of liquid contained within the treated tissue disposed within the container or package. Preferably, the treated dry tissue component, valve assembly or bioprosthetic valve made therefrom is placed into a microorganism-resistant package. An example of a packaged tissue valve ready for reconstitution includes a package having an outer periphery that defines an inner space. The inner space has an environment that is substantially dry and sterile. The tissue valve includes a support configured to fit within the inner space of the package and a vacuum-dried or lyophilized valve assembly attached to the support. The dry tissue valve is encased within the package. In one embodiment, the package with the dry tissue valve may also include a delivery device. In another embodiment, the dry tissue valve may be preloaded within the delivery device within the package.

After the dry tissue component, valve assembly or bioprosthetic valve has been placed in the inner space of the package, the package may be sealed. The sealed package may then be sterilized, such as by a gas sterilization process or by exposure to ionizing radiation. The gas sterilization process involves exposure to a gas including, but not limited to, ethylene oxide and peracetic acid. The ionizing radiation can be gamma irradiation or electron beam irradiation. To ensure the inner space remains sterile following sterilization, the package is preferably formed from a material, such as Tyvek® (E.I. DuPont de Nemours and Company) or Mylar® (DuPont Teijin Films U.S.), which is impenetrable to microorganisms such as bacteria and fungi.

An example of a conventional procedure for sterilization by exposure to ethylene oxide involves exposure of the package to a mixture of 10 wt % ethylene oxide and 90 wt % hydrochlorofluorocarbon at a chamber pressure of about 8 to about 10 psi and a temperature of about 38° C. for about 24 hours, or a temperature of about 54-57° C. for about 130 minutes. In one embodiment, the package may be exposed to 100 wt % of ethylene oxide gas at a chamber pressure of about 1.3 psi, a relative humidity of about 50% and a temperature of about 40° C. for about 12 hours.

In one preferred embodiment, the sealed package may be sterilized by exposure to peracetic acid gas. The mechanism of action of peracetic acid is thought to be similar to other oxidizing agents, i.e., it denatures proteins, disrupts cell wall permeability, and oxidizes sulfhydral and disulfide bonds in proteins, enzymes, and other metabolites. The peracetic acid vapor interacts with numerous cellular constituents, breaking them down and inactivating routine functionality. With the disintegration of the bacterial cell wall, internal components will no longer be contained and are unable to organize. Proteins are rapidly attacked by peracetic acid through oxidation of amino acids to carbonyls, particularly tryptophan, cysteine and methionine. Sterilization by peracetic acid can be performed in a chamber of 500 Torr at room temperature (18-30° C.) for a short period of time, for example, a few seconds to a few hours. Compared to conventional sterilization by ethylene oxide, gamma irradiation or electron beam irradiation, peracetic acid sterilization provides high compatibility with materials, low temperature operation that does not affect the product or packaging, low or no residuals, safety to use for operators, and short processing times.

The resulting product is a substantially sterile tissue component, valve assembly or implantable tissue or bioprosthetic valve suitable for dry storage. The sterile bioprosthetic tissue valve prepared in accordance with the present methods may be well-suited for implantation into patients with cardiovascular diseases. As used herein, the term "patient" means any mammals such as, for example, humans, dogs, cats, horses, and non-human primates. Prior to use, the bioprosthetic valve is removed from the package, and the tissue portion thereof may be rehydrated by exposure to an aqueous solution, preferably a sterile saline solution, such as a sterile 0.9 wt % aqueous saline solution. In some instances, the tissue portion may be rehydrated by rinsing with a sterile 0.9 wt % aqueous saline solution for about two to about ten seconds, and the valve may then be loaded into or onto a delivery device. When a substantially sterile tissue component or valve assembly is stored in the package, the tissue component or valve assembly may be rehydrated using the same technique as for the bioprosthetic valve, after which the tissue component or valve assembly may be assembled to a support to form a bioprosthetic valve.

Rehydration or reconstitution of the vacuum-dried or lyophilized tissue before use may be a complete reconstitution in which the moisture content of the tissue is roughly equivalent to the moisture content the tissue would have when in equilibrium with the patient's biofluid in situ. In such circumstances, and in some embodiments, the delivery device may be configured to accommodate a resulting increase in the volume of the rehydrated bioprosthetic valve, if needed.

In one embodiment, the tissue valve comprises a vacuum-dried or lyophilized valve assembly attached to a stent that is capable of being resheathed, with the resulting tissue valve loaded onto a delivery device which permits resheathing. The stent and the valve assembly are configured cooperatively such that the valve assembly can be exposed when on the delivery device, reconstituted, sheathed/resheathed and/or implanted. This allows the surgical team to expose the valve assembly for reconstitution prior to implantation. In a further aspect of this embodiment, the stent may be structured such that the valve assembly can be exposed for reconstitution. In another embodiment, a bioprosthetic valve may be partially preloaded onto a delivery device to allow rehydration. In a further embodiment, a bioprosthetic valve which is not preloaded onto a delivery device may be reconstituted and thereafter crimped and loaded onto a delivery device.

In another embodiment, the valve assembly may be reconstituted while fully sheathed. Reconstitution while fully sheathed may be achieved by irrigating an aqueous solution through the delivery device prior to implantation.

Described herein are methods of preparing bioprosthetic tissue or a bioprosthetic device comprising the same so as to have strong calcification resistance and allow for sterilization and storage in a non-toxic environment without causing damage to the tissue. The methods comprise fixing the tissue, treating the fixed tissue with an alcohol solution and subsequently with a polyol solution, air-drying or vacuum-drying of the alcohol/polyol-treated fixed tissue, and sterilizing the dried tissue. As a result, tissue treated in accordance with the present methods can be returned to a size that is at least about 90%, preferably at least about 95%, more preferably at least about 98%, of its original hydrated size following rehydration in sterile saline for about 10 seconds. Tissue prepared in accordance with the present methods is therefore well-suited for use in a bioprosthetic valve.

The following examples are for purpose of illustration only and are not intended to limit the scope of the disclosure as defined in the claims hereinafter.

Bovine pericardial tissue that was freshly pre-fixed with 0.5 v/v % of gluaraldehyde in a PBS buffer was used in the test groups set forth below.

Test Group 1

The pre-fixed tissue was sterilized by a typical process according to a manufacturing standard, rinsed with a sterile 0.9 wt % aqueous saline solution for about 20 minutes, and preserved in a 0.5 v/v % formaldehyde phosphate-buffered solution. Before implantation, ten tissue specimens were removed from the 0.5 v/v % formaldehyde phosphate-buffered preservation solution, and rinsed with a sterile 0.9 wt % aqueous saline solution for 2-10 seconds. Test Group 1 was for a positive calcium control.

Test Group 2

The pre-fixed tissue was sterilized by a typical process according to a manufacturing standard, and rinsed with a sterile 0.9 wt % aqueous saline solution for about 20 minutes. Ten resulting tissue specimens were then immersed in a 95 v/v % ethanol aqueous solution for about 24 hours. The tissue specimens were removed from the ethanol solution and rinsed with a sterile 0.9 wt % aqueous saline solution for about 20 minutes. The tissue specimens were then stored in a 0.5 v/v % formaldehyde phosphate-buffered solution. Before implantation, tissue specimens were removed from the 0.5 v/v % formaldehyde phosphate-buffered preservation solution and rinsed with a sterile 0.9 wt % aqueous saline solution for 2-10 seconds.

Test Group 3

The pre-fixed tissue was sterilized by a typical process according to a manufacturing standard, and rinsed with a sterile 0.9 wt % aqueous saline solution for about 20 minutes. Ten resulting tissue specimens were then immersed in a 95 v/v % ethanol aqueous solution for about 24 hours. The tissue specimens were removed from the ethanol solution and rinsed with a sterile 0.9 wt % aqueous saline solution for about 20 minutes. The tissue specimens were subsequently immersed in a 50 v/v % glycerol in a 0.9 wt % aqueous saline solution for about 24 to about 26 hours. The tissue specimens were removed from the glycerol solution and then air-dried at room temperature of about 25° C. for about 16 to about 24 hours. The dried tissue specimens were put in a jar sealed with a Tyvek® membrane for sterilization. The sealed jar was exposed to 100 wt % of ethylene oxide (EO) gas at a chamber pressure of about 1.3 psi and relative humidity of about 50% and a temperature of about 40° C. for about 12 hours. The tissue specimens were stored in the jar at ambient conditions. Before implantation, the valve specimens were rinsed with a sterile 0.9 wt % aqueous saline solution for 2-10 seconds.

Test Group 4

Ten tissue specimens were prepared according to Test Group 3, except that before implantation, the tissue specimens were not rinsed.

Test Group 5

Ten tissue specimens were prepared according to Test Group 3, except that the dried tissue specimens were put in a jar sealed with a Mylar® membrane for sterilization with peracetic acid (PAA). The jar was exposed to 100 wt % of peracetic acid gas at a chamber pressure of about 500 Torr at room temperature of about 25° C. for about 15 minutes.

Test Group 6

Ten tissue specimens were prepared according to Test Group 5, except that before implantation, the tissue specimens were not rinsed.

The preparation of the specimens for Test Groups 1-6 are summarized in Table 1 as follows:

TABLE 1

Processes for Test Groups 1-6

| Test Group # | Sample Numbers | Anti-calcification Treatment | Drying | Terminal Sterilization Method | Pre-Implant Rinse |
|---|---|---|---|---|---|
| 1 | 10 | None | None | None | Yes |
| 2 | 10 | Ethanol | None | None | Yes |
| 3 | 10 | Ethanol/Glycerol | Yes | EO | Yes |
| 4 | 10 | Ethanol/Glycerol | Yes | EO | No |
| 5 | 10 | Ethanol/Glycerol | Yes | PAA | Yes |
| 6 | 10 | Ethanol/Glycerol | Yes | PAA | No |

The tissue specimens of Test Groups 1-6 were then implanted into a subcutaneous pocket in 3-4 week old Sprague-Dawley rats. At the end of a period of 63 days, the tissue specimens were collected and examined for calcification by quantitative analyses of calcium and phosphorus using Inductively Coupled Plasma Optical Emission Spectrometry (ICP-OES). The mean calcium results are summarized in Table 2 below and in FIG. 1.

TABLE 2

ICP Calcium Results

| Test Group # | Sample Numbers | Mean Calcium (mg/g) |
| --- | --- | --- |
| 1 | 10 | 193.31 ± 18.30 |
| 2 | 10 | 2.14 ± 6.35 |
| 3 | 10 | 0.11 ± 0.01 |
| 4 | 10 | 10.89 ± 34.11 |
| 5 | 10 | 23.40 ± 43.14 |
| 6 | 10 | 9.49 ± 29.69 |

*data represented as mean +/− one standard deviation

Table 2 and FIG. 1 demonstrate that a two-step treatment of bioprosthetic tissue first with ethanol followed by glycerol greatly minimizes the calcification.

Figure 2:
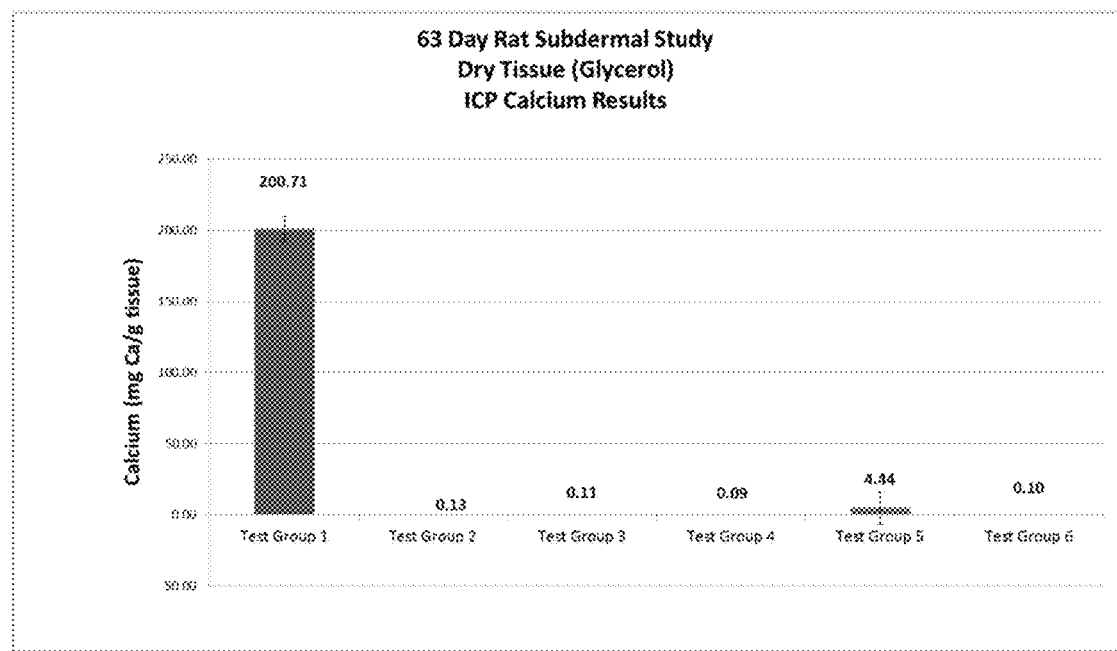
FIG. 2 is a bar graph depicting the mean calcium of Test Groups 1-6 with the folded samples removed in a 63-day rat subdermal study.

Several of the test specimens were identified as folded during sample recovery at term. Folded tissue can potentially cause stress-induced calcification and increase the variability in the test results. Approximately 40% of the folded test samples were calcified, and 100% of the folded samples were calcified in both Test Group 1 (control group) and Test Group 2. Because the calcium in these samples was likely related to the folded (stressed) condition of the samples, the folded sample results (including samples that did not calcify) were removed as "outliers" and the data was re-evaluated. The mean calcium results are summarized in Table 3 below and in FIG. 2:

TABLE 3

ICP Calcium Results

| Test Group # | Sample Numbers | Mean Calcium (mg/g) |
| --- | --- | --- |
| 1 | 8 | 200.71 ± 8.62 |
| 2 | 9 | 0.13 ± 0.02 |
| 3 | 9 | 0.11 ± 0.01 |
| 4 | 8 | 0.09 ± 0.01 |
| 5 | 7 | 4.44 ± 11.49 |
| 6 | 6 | 0.10 ± 0.01 |

*data represented as mean +/− one standard deviation

It is interesting to note that the majority of folded samples did not calcify in Test Groups 3-6. The two-step ethanol/glycerol process used for Test Groups 3-6 may help reduce stress-induced calcification.

To summarize the foregoing description, a method of preparing calcification-resistant tissue includes providing fresh biological tissue; cross-linking the tissue to produce fixed tissue; treating the fixed tissue with an alcohol for a time sufficient to allow the alcohol to be diffused into the tissue to produce alcohol-treated fixed tissue; and treating the alcohol-treated fixed tissue with a polyol for a time sufficient to allow fluid in the tissue to be replaced by the polyol to produce alcohol/polyol-treated fixed tissue; and/or the method may further include storing the alcohol/polyol-treated fixed tissue in an aqueous solution; and/or the method may further include sterilizing the alcohol/polyol-treated fixed tissue in a solution comprising propylene oxide or peracetic acid; and/or the method may further include drying the alcohol/polyol-treated fixed tissue to produce dried tissue, and storing the dried tissue in a dry, ambient environment; and/or the method may further include placing the dried tissue in a package and sealing the package; and/or the method may further include sterilizing the fixed tissue in a solution comprising propylene oxide or peracetic acid prior to the step of treating the fixed tissue with the alcohol; and/or the method may further include sterilizing the package after the sealing step; and/or the sterilization step may be performed by exposing the sealed package to ethylene oxide or peracetic acid; and/or the cross-linking step may be performed by using a glutaraldehyde or formaldehyde aqueous solution; and/or the alcohol may be a lower aliphatic (C1 to C8) alcohol, or a combination of lower aliphatic alcohols; and/or the alcohol may be ethanol; and/or the alcohol may be in an aqueous solution comprising from about 85 v/v % to about 100 v/v % of alcohol; and/or the aqueous solution may have a volume sufficient to submerge the tissue; and/or the alcohol may be an aqueous solution comprising 95 v/v % of alcohol; and/or the step of treating the fixed tissue with an alcohol may be performed for about 12 hours to about 48 hours; and/or the step of treating the fixed tissue with an alcohol may be performed for at least 24 hours; and/or the step of treating the fixed tissue with an alcohol may be performed at a temperature between about 15° C. and about 30° C.; and/or the polyol may be a lower aliphatic diol or triol (C1 to C4), or a combination of lower aliphatic diols or triols; and/or the polyol may be glycerol; and/or the polyol may be in water or in a 0.9 wt % aqueous saline solution comprising from about 20 v/v % to about 100 v/v % of polyol; and/or the polyol may be in a 0.9 wt % aqueous saline solution to produce a polyol/saline solution comprising about 50 v/v % of polyol; and/or the polyol/saline solution may have a volume sufficient to submerge the tissue; and/or the step of treating the alcohol-treated fixed tissue with a polyol may be performed for about 12 hours to about 48 hours; and/or the step of treating the alcohol-treated fixed tissue with a polyol may be performed for at least 24 hours; and/or the step of treating the alcohol-treated fixed tissue with a polyol may be performed at a temperature between about 15° C. and about 30° C.; and/or the tissue may be in the form of a tissue component, a valve assembly for a bioprosthetic valve or a fully assembled bioprosthetic valve incorporating the tissue; and/or the tissue component may be a tissue patch for use in cardiac repairs; and/or the prosthetic valve may be a prosthetic heart valve; and/or the prosthetic heart valve may be a surgical heart valve; and/or the prosthetic heart valve may be a collapsible transcatheter heart valve.

The present application also discloses tissue prepared by the described methods, and a valve assembly for a bioprosthetic valve or a fully assembled bioprosthetic valve incorporating the tissue.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A method of preparing calcification-resistant tissue, comprising:
   providing fresh biological tissue;
   cross-linking the tissue to produce fixed tissue;
   treating the fixed tissue with an alcohol for a time sufficient to allow the alcohol to be diffused into the tissue to produce alcohol-treated fixed tissue; and
   treating the alcohol-treated fixed tissue with a polyol for a time sufficient to allow fluid in the tissue to be replaced by the polyol to produce alcohol/polyol-treated fixed tissue,
   wherein the alcohol is at least one of a lower aliphatic ($C_1$ to $C_8$) alcohol, and the alcohol is in an aqueous solution comprising from about 85 v/v % to about 100 v/v % of the alcohol.

2. The method of claim 1, further comprising sterilizing the fixed tissue in a solution comprising propylene oxide or peracetic acid prior to the step of treating the fixed tissue with the alcohol.

3. The method of claim 1, further comprising sterilizing the alcohol/polyol-treated fixed tissue in a solution comprising propylene oxide or peracetic acid.

4. The method of claim 1, further comprising:
   drying the alcohol/polyol-treated fixed tissue to produce dried tissue; and
   storing the dried tissue in a dry, ambient environment.

5. The method of claim 4, further comprising placing the dried tissue in a package and sealing the package.

6. The method of claim 5, further comprising sterilizing the package after the sealing step.

7. The method of claim 6, wherein the sterilization step is performed by exposing the sealed package to ethylene oxide or peracetic acid.

8. The method of claim 1, wherein the cross-linking step is performed by using a glutaraldehyde or formaldehyde aqueous solution.

9. The method of claim 1, wherein the alcohol is ethanol.

10. The method of claim 1, wherein the step of treating the fixed tissue with an alcohol is performed at a temperature between about 15° C. and about 30° C.

11. The method of claim 1, wherein the polyol is at least one of a lower aliphatic diol or triol ($C_1$ to $C_4$).

12. The method of claim 1, wherein the polyol is glycerol.

13. The method of claim 1, wherein the polyol is in water or a 0.9 wt % aqueous saline solution comprising from about 20 v/v % to about 100 v/v % of polyol.

14. The method of claim 1, wherein the step of treating the alcohol-treated fixed tissue with a polyol is performed at a temperature between about 15° C. and about 30° C.

15. The method of claim 1, wherein the tissue is in the form of a tissue component, a valve assembly for a bioprosthetic valve or a fully assembled bioprosthetic valve incorporating the tissue.

16. Tissue prepared according to the method of claim 1.

17. A method of preparing calcification-resistant tissue, comprising:
   providing fresh biological tissue;
   cross-linking the tissue to produce fixed tissue;
   treating the fixed tissue with an alcohol for a time sufficient to allow the alcohol to be diffused into the tissue to produce alcohol-treated fixed tissue; and
   treating the alcohol-treated fixed tissue with a polyol for a time sufficient to allow fluid in the tissue to be replaced by the polyol to produce alcohol/polyol-treated fixed tissue,
   wherein the step of treating the fixed tissue with an alcohol is performed for about 12 hours to about 48 hours.

18. The method of claim 17, wherein the alcohol is at least one of a lower aliphatic ($C_1$ to $C_8$) alcohol.

19. The method of claim 17, wherein the alcohol is in an aqueous solution comprising from about 85 v/v % to about 100 v/v % of alcohol.

20. The method of claim 17, wherein the polyol is at least one of a lower aliphatic diol or triol ($C_1$ to $C_4$).

21. A method of preparing calcification-resistant tissue, comprising:
   providing fresh biological tissue;
   cross-linking the tissue to produce fixed tissue;
   treating the fixed tissue with an alcohol for a time sufficient to allow the alcohol to be diffused into the tissue to produce alcohol-treated fixed tissue; and
   treating the alcohol-treated fixed tissue with a polyol for a time sufficient to allow fluid in the tissue to be replaced by the polyol to produce alcohol/polyol-treated fixed tissue,
   wherein the step of treating the alcohol-treated fixed tissue with a polyol is performed for about 12 hours to about 48 hours.

22. The method of claim 21, wherein the alcohol is at least one of a lower aliphatic ($C_1$ to $C_8$) alcohol.

23. The method of claim 21, wherein the polyol is at least one of a lower aliphatic diol or triol ($C_1$ to $C_4$).

* * * * *